United States Patent
Lee et al.

(10) Patent No.: US 10,034,630 B2
(45) Date of Patent: Jul. 31, 2018

(54) APPARATUS AND METHOD TO TRAIN AUTONOMOUS DRIVING MODEL, AND AUTONOMOUS DRIVING APPARATUS

(71) Applicant: Samsung Electronics Co., Ltd., Suwon-si (KR)

(72) Inventors: Dong Hwa Lee, Hwaseong-si (KR); Chang Hyun Kim, Seongnam-si (KR); Eun Soo Shim, Suwon-si (KR); Ki Hwan Choi, Yongin-si (KR); Hyun Jin Choi, Seoul (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 0 days.

(21) Appl. No.: 15/351,629

(22) Filed: Nov. 15, 2016

(65) Prior Publication Data
US 2017/0135621 A1     May 18, 2017

(30) Foreign Application Priority Data
Nov. 16, 2015   (KR) .................. 10-2015-0160725

(51) Int. Cl.
*A61B 5/18*      (2006.01)
*A61B 3/10*      (2006.01)
(Continued)

(52) U.S. Cl.
CPC .............. *A61B 5/18* (2013.01); *A61B 3/0025* (2013.01); *A61B 3/10* (2013.01); *B60W 30/00* (2013.01);
(Continued)

(58) Field of Classification Search
CPC ...... A61B 5/18; G05D 1/0246; G05D 1/0221; G05D 1/0214; G05B 19/4182;
(Continued)

(56) References Cited

U.S. PATENT DOCUMENTS

| 5,724,489 A | * | 3/1998 | Yamamoto ......... G05B 19/4182 700/245 |
| 7,647,152 B2 | | 1/2010 | Ogawa |

(Continued)

FOREIGN PATENT DOCUMENTS

| JP | 2014-115168 A | 6/2014 |
| KR | 10-2012-0128423 A | 11/2012 |

(Continued)

OTHER PUBLICATIONS

Chen, C. et al., "Deepdriving: Learning affordance for direct perception in autonomous driving," Proceedings of the IEEE International Conference on Computer Vision, 2015 (9 pages in English).

(Continued)

*Primary Examiner* — Yuri Kan
(74) *Attorney, Agent, or Firm* — NSIP Law

(57) ABSTRACT

Disclosed is an apparatus and method to train an autonomous driving model. The apparatus includes a driver information collection processor configured to collect driver information while a vehicle is being driven. The apparatus also includes a sensor information collection processor configured to collect sensor information from a sensor installed in the vehicle while the vehicle is being driven, and a model training processor configured to train the autonomous driving model based on the driver information and the sensor information.

25 Claims, 9 Drawing Sheets

(51) Int. Cl.
*A61B 3/00* (2006.01)
*B60W 30/00* (2006.01)
*G05D 1/02* (2006.01)
*G06N 3/04* (2006.01)
*A61B 5/024* (2006.01)
*A61B 5/0402* (2006.01)
*A61B 5/0476* (2006.01)
*A61B 5/22* (2006.01)

(52) U.S. Cl.
CPC ......... *G05D 1/0221* (2013.01); *G06N 3/0454* (2013.01); *A61B 5/024* (2013.01); *A61B 5/0402* (2013.01); *A61B 5/0476* (2013.01); *A61B 5/225* (2013.01)

(58) Field of Classification Search
CPC ........... G06F 17/3028; G06K 9/00845; B60W 30/08; B64C 39/024
See application file for complete search history.

(56) References Cited

U.S. PATENT DOCUMENTS

| | | | |
|---|---|---|---|
| 8,280,602 B2 | 10/2012 | Uechi et al. | |
| 8,665,099 B2 | 3/2014 | Namba et al. | |
| 8,965,621 B1* | 2/2015 | Urmson | G05D 1/0214 701/23 |
| 9,443,153 B1* | 9/2016 | Gupta | G06F 17/3028 |
| 2006/0149428 A1* | 7/2006 | Kim | A61B 5/18 701/1 |
| 2013/0231824 A1* | 9/2013 | Wilson | G05D 1/0246 701/26 |
| 2013/0325202 A1* | 12/2013 | Howard | B60W 30/08 701/1 |
| 2014/0204193 A1 | 7/2014 | Zhang et al. | |
| 2015/0019058 A1 | 1/2015 | Georgiev | |
| 2015/0025748 A1 | 1/2015 | Hagnander et al. | |
| 2015/0166069 A1* | 6/2015 | Engelman | B60W 30/12 701/23 |
| 2016/0068267 A1* | 3/2016 | Liu | B64C 39/024 701/11 |
| 2016/0210382 A1* | 7/2016 | Alaniz | G05D 1/0221 |
| 2017/0124407 A1* | 5/2017 | Micks | G06K 9/00845 |

FOREIGN PATENT DOCUMENTS

| | | |
|---|---|---|
| KR | 10-1327116 B1 | 11/2013 |
| KR | 10-2014-0038629 A | 3/2014 |
| KR | 10-2015-0066303 A | 6/2015 |

OTHER PUBLICATIONS

Pomerleau, D., "Alvinn: An autonomous land vehicle in a neural network," Carnegie-Mellon Univ Pittsburgh PA Artificial Intelligence and Psychology Project, No. AIP-77, 1989 (9 pages in English).

* cited by examiner

APPARATUS AND METHOD TO TRAIN AUTONOMOUS DRIVING MODEL, AND AUTONOMOUS DRIVING APPARATUS

CROSS-REFERENCE TO RELATED APPLICATION(S)

This application claims priority from Korean Patent Application No. 10-2015-0160725, filed on Nov. 16, 2015, in the Korean Intellectual Property Office, the disclosure of which is incorporated herein by reference in its entirety.

BACKGROUND

1. Field

The following description relates to an apparatus and a method to train an autonomous driving model in an environment with real-driving environment data and an autonomous driving apparatus and method using the autonomous driving model.

2. Description of Related Art

A general autonomous driving vehicle drives autonomously by recognizing and assessing an ambient environment using various sensors attached to the vehicle. Such an autonomous driving vehicle recognizes an individual object in the ambient environment using various sensors such as a camera, a light detection and ranging (lidar), and a radar installed for environment recognition during driving. In order to learn the recognized individual object, the autonomous driving vehicle performs a task of labeling ground truth data of the object.

However, each of the sensors installed in the vehicle has a limited recognition range and low reliability problem. Accordingly, there are limitations in autonomous driving technology that depends only on sensors installed in a vehicle. Furthermore, there are difficulties in defining autonomous driving rules for all surrounding conditions because a real-road driving environment is very complicated.

SUMMARY

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

In accordance with an embodiment, there is provided an apparatus to train an autonomous driving model, the apparatus may include: a driver information collection processor configured to collect driver information while a vehicle is being driven; a sensor information collection processor configured to collect sensor information from a sensor installed in the vehicle while the vehicle is being driven; and a model training processor configured to train the autonomous driving model based on the driver information and the sensor information.

The vehicle is driven in at least one of a real-road driving situation and a virtual driving situation.

The driver information may also include at least one of driver state information, driver behavior information, and driving pattern information.

The driver state information may also include at least one of information about a gaze direction, a heart rate, an electrocardiogram, and brain waves of a driver, and grip strength of the driver's hand holding a steering wheel. The driver behavior information may also include at least one of information about manipulation of a stereo device, air conditioning device, a mirror device, and a navigation device installed in the vehicle, and the driving pattern information may also include at least one of information about a steering wheel manipulation information, horn manipulation information, turn-signal manipulation information, emergency button manipulation information, and brake pedal manipulation information.

The model training processor may train the autonomous driving model to learn about a driving area based on information about the gaze direction of the driver and trains the autonomous driving model to learn at least one of a dangerous situation and a level of danger in driving based on the driving pattern information.

The apparatus may also include: a navigation information collection processor configured to collect navigation setting information may include information on a starting location and an ending location.

The model training processor may train the autonomous driving model to learn about an integrated driving situation from the starting location to the ending location and based on the navigation setting information.

The sensor information may also include at least one of surrounding image information, surrounding voice information, current location information, light detection and ranging (lidar) sensor information, radar sensor information, vehicle speed information, and acceleration information.

The autonomous driving model may be based on a deep neural network configured to learn spatial information and temporal information.

In accordance with an embodiment, there is provided a method to train an autonomous driving model, the method may include: collecting driver information while a vehicle is being driven; collecting sensor information from a sensor installed in the vehicle while the vehicle is being driven; and training the autonomous driving model based on the driver information and the sensor information.

The driver information may also include at least one of driver state information, driver behavior information, and driving pattern information.

The driver state information may also include at least one of information about a gaze direction, a heart rate, an electrocardiogram, and brain waves of a driver, and grip strength of the driver's hand holding a steering wheel.

The driver behavior information may also include at least one of information about manipulation of a stereo device, air conditioning device, a mirror device, and a navigation device installed in the vehicle, and the driving pattern information may also include at least one of a steering wheel manipulation information, horn manipulation information, turn-signal manipulation information, emergency button manipulation information, and brake pedal manipulation information.

The training of the model may also include training the autonomous driving model to learn about a driving area based on information about the gaze direction of the driver and training the autonomous driving model to learn about at least one of a dangerous situation and a level of danger in driving based on the driving pattern information.

The method may also include: collecting navigation setting information may include information on a starting location and an ending location.

The training of the model may also include training the autonomous driving model to learn about an integrated driving situation from the starting location to the ending location further based on the navigation setting information.

The sensor information may also include at least one of surrounding image information, surrounding voice information, current location information, light detection and ranging (lidar) sensor information, radar sensor information, vehicle speed information, and acceleration information.

In accordance with an embodiment, there is provided a non-transitory computer-readable storage medium storing instructions that, when executed by a processor, cause the processor to perform the method described above.

In accordance with another embodiment, there is provided an autonomous driving apparatus, may include: a driving information collection processor configured to collect vehicle driving information may include at least one of driver information, sensor information, and navigation setting information while a vehicle is being driven; and a command processor configured to train an autonomous driving model installed in the vehicle or autonomously drive the vehicle based on the collected driving information.

The autonomous driving apparatus may also include: a command receiver configured to receive an autonomous driving command from a driver.

The command processing processor may also include: a model determination processor configured to determine whether the autonomous driving model is appropriate for a driver and the current driving situation based on either one or both of the driver information and the navigation setting information; a model training processor configured to retrain the autonomous driving model based on the collected driving information upon determining that the autonomous driving model is inappropriate; and a driving control processor configured to automatically control operation of the vehicle using the collected driving information and the autonomous driving model upon determining that the autonomous driving model is appropriate.

The model determination processor may check whether the autonomous driving model is trained to learn about the driver based on the driver information and determines that the autonomous driving model is inappropriate upon determining that the autonomous driving model is untrained about the driver.

The model determination processor may check whether the autonomous driving model is trained to learn about a driving route from a starting location to an ending location based on the navigation setting information and determines that the autonomous driving model is inappropriate upon determining that the autonomous driving model is untrained about the driving route.

In accordance with a further embodiment, there is provided an apparatus, may include: a processor configured to collect driver information corresponding to behavior information of a driver driving a vehicle, virtually or in real-time, collect sensor information from sensors capturing either one or both of image and ambient information surrounding the vehicle and vehicle operational parameters corresponding to either one or both of a current driving route and current driving conditions, train an autonomous driving model by combining the driver information and the sensor information, and execute the autonomous driving model upon determining that the trained autonomous driving model corresponds to at least one of the driver, the current driving route.

The processor may also include: a driver information collection processor configured to collect the driver information, a sensor information collection processor configured to collect the sensor information corresponding to either one or both of the current driving route and the current driving conditions, a model training processor configured to train the autonomous driving model, and a driving control processor configured to execute the autonomous driving model upon determining that the trained autonomous driving model corresponds to at least one of the driver, the current driving route.

The apparatus may also include: a navigation information collection processor configured to collect navigation setting information may include information regarding a starting location, a stopover location, and an ending location.

The processor may be further configured to check whether the autonomous driving model has been trained within a preset period of time to prevent a retraining of the autonomous driving model.

Other features and aspects will be apparent from the following detailed description, the drawings, and the claims.

Figure 1:
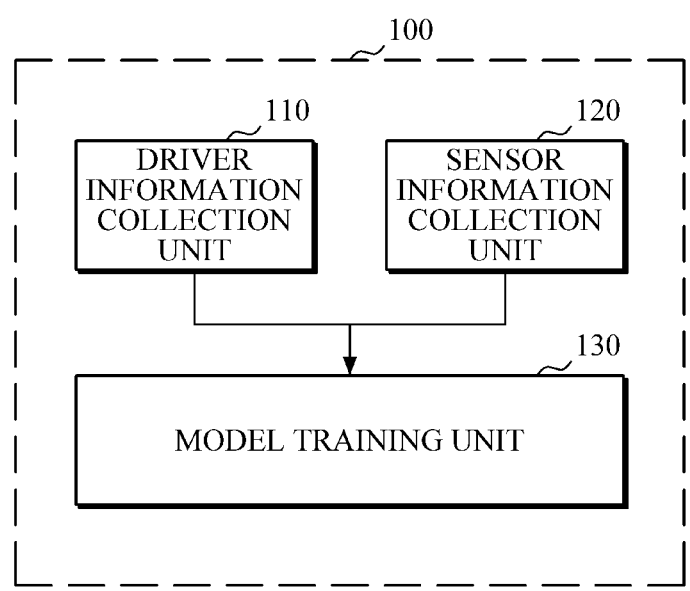
FIG. 1 is a block diagram of an apparatus to train an autonomous driving model, according to an embodiment.

Throughout the drawings and the detailed description, unless otherwise described, the same drawing reference numerals should be understood to refer to the same elements, features, and structures. The relative size and depiction of these elements may be exaggerated for clarity, illustration, and convenience.

DETAILED DESCRIPTION

The following detailed description is provided to assist the reader in gaining a comprehensive understanding of the methods, apparatuses, and/or systems described herein. However, various changes, modifications, and equivalents of the methods, apparatuses, and/or systems described herein will be apparent after an understanding of the disclosure of this application. For example, the sequences of operations described herein are merely examples, and are not limited to those set forth herein, but may be changed as will be apparent after an understanding of the disclosure of this application, with the exception of operations necessarily occurring in a certain order. Also, descriptions of features that are known in the art may be omitted for increased clarity and conciseness.

The features described herein may be embodied in different forms, and are not to be construed as being limited to the examples described herein. Rather, the examples described herein have been provided merely to illustrate some of the many possible ways of implementing the methods, apparatuses, and/or systems described herein that will be apparent after an understanding of the disclosure of this application.

As used herein, the term "and/or" includes any one and any combination of any two or more of the associated listed items.

The terminology used herein is for describing various examples only, and is not to be used to limit the disclosure. The articles "a," "an," and "the" are intended to include the plural forms as well, unless the context clearly indicates otherwise. The terms "comprises," "includes," and "has" specify the presence of stated features, numbers, operations, members, elements, and/or combinations thereof, but do not preclude the presence or addition of one or more other features, numbers, operations, members, elements, and/or combinations thereof.

Due to manufacturing techniques and/or tolerances, variations of the shapes shown in the drawings may occur. Thus, the examples described herein are not limited to the specific shapes shown in the drawings, but include changes in shape that occur during manufacturing.

The features of the examples described herein may be combined in various ways as will be apparent after an understanding of the disclosure of this application. Further, although the examples described herein have a variety of configurations, other configurations are possible as will be apparent after an understanding of the disclosure of this application.

Details of other embodiments are included in the detailed description and drawings. Advantages and features of the described technique, and implementation methods thereof will be clarified through following embodiments described with reference to the accompanying drawings. Like reference numerals refer to like elements throughout.

An apparatus and method to train an autonomous driving model, according to embodiments, will be described below in detail with reference to the accompanying drawings. An autonomous driving model training apparatus, according to some embodiments, refers to a structural apparatus to train a model for context awareness and operation determination (hereinafter referred to as an "autonomous driving model") to autonomously drive a vehicle using a variety of information associated with different driving situations. For example, the autonomous driving model may be based on a neural network, but is not limited thereto.

In addition, the autonomous driving model training apparatus may be installed in a driving vehicle in order to train and produce an autonomous driving model. Alternatively, the autonomous driving model training apparatus may be implemented in a separate hardware device wired or wirelessly connected to a vehicle to collect information to train the autonomous driving model over a network instead of being installed in the vehicle. In this case, the autonomous driving model training apparatus wire or wirelessly receives the collected information from the vehicle to train the autonomous driving model.

FIG. 1 is a block diagram of an autonomous driving model training apparatus, according to an embodiment.

Referring to FIG. 1, an autonomous driving model training apparatus 100 includes a driver information collection processor 110, a sensor information collection processor 120, and a model training processor 130.

In order to train an autonomous driving model, the driver information collection processor 110 collects a variety of information as training data that is associated with a driver while driving a vehicle, that is, vehicle driving situation, and driver information. In an example, the vehicle driving situation includes a situation in which the driver is actually driving the vehicle on a road and also a situation in which the driver is virtually driving the vehicle in a virtual situation that is set similar to a real road situation. Another vehicle driving situation may be defined based on a time of the day or night that the driver is driving the vehicle, the road conditions, such as paved roads or rough terrain, age of the driver, and ambient/environmental conditions, such as severe winds, rain, fog, dark, or sunny day. In addition, the vehicle driving situation may refer to a period from the time at which a driver gets in the vehicle to the time at which the driver stops driving and gets off the vehicle.

As an example, the driver information may include driving pattern information regarding a driving pattern in which the driver responds to surrounding road conditions the driver is facing while driving. For example, the driving pattern information includes information associated with a manner in which the driver drives the vehicle such as steering wheel manipulation information, accelerator pedal manipulation information, horn manipulation information, turn-signal lamp manipulation information, emergency button manipulation information, and brake pedal manipulation information according to various road conditions such as road curvature, a sudden accident, a rumble strip area, a crosswalk, a traffic signal change, and a traffic congestion.

As another example, the driver information includes driver behavior or behavioral information regarding behavior the driver casually or habitually exhibits while driving, irrespective of the surrounding road conditions. For example, the driver behavior information includes manipulation information regarding an audio device including a stereo system, an air conditioning device such as an air conditioner, and a mirror device such as a side mirror and a room mirror, navigation manipulation information, etc.

As another example, the driver information includes driver state information that indicates states of the driver corresponding to various surrounding situations or specific behaviors exhibited by the driver. For example, the driver state information includes a gaze direction, a heart rate, an electrocardiogram, and brain waves of a driver, and grip strength of the driver's hand holding a steering wheel.

The sensor information collection processor 120 collects a variety of information associated with the driving of a vehicle from various sensors installed in a vehicle. For example, the sensor information collection processor 120 collects image information regarding road conditions, light detection and ranging (lidar) sensor information, radar sensor information, and vehicle operational parameters such as speed information and acceleration information captured through a camera module, a black box, a distance measurement sensor, a lidar sensor, a radar sensor, a speed sensor, and an acceleration sensor.

When the driver information, the vehicle driving situation, and the sensor information are collected to train the autonomous driving model, the model training processor 130 trains the autonomous driving model in consideration of all of the collected driver information and sensor information. In this case, the model training processor 130 creates training data by combining two or more pieces of the collected the driver information, the vehicle driving situation, and the sensor information and trains the autonomous driving model using the created training data.

As an example, in order to train the autonomous driving model to learn about an area in which the driver has to be careful while driving, the model training processor 130 uses gaze direction information of the driving state information as the training data. In this case, the model training processor 130 creates training data regarding the area in which the driver has to be careful by analyzing an image in the gaze direction in which the driver keeps his/her eyes in additional consideration of surrounding image information of the sensor information.

As another example, the model training processor 130 processes the driving pattern information and/or the driver state information to create training data regarding dangerous situations and levels of danger in driving and may train the autonomous driving model using the created training data. For example, in order to create the training data for dangerous situations and considering various levels of danger, the model training processor 130 analyzes how much grip strength a driver has in holding a steering wheel, whether the driver pushed an emergency lamp button, how much the driver's heart rate is, or how strongly the driver presses a brake pedal in various driving situations such as a sudden accident, a curved road, a sudden signal change, and a sudden stop. In this case, the model training processor 130 determines the various driving situations considering whether the current road is curved or whether a traffic signal has changed by analyzing the sensor information, for example, the surrounding image information.

However, this is merely illustrative, and thus embodiments are not limited thereto. The model training processor 130 may create the training data used to train, considering various situations, needed for the autonomous driving of a vehicle or various situations associated with operations of the vehicle to be controlled by processing various information collected while the vehicle is being driven on a road.

Figure 2:
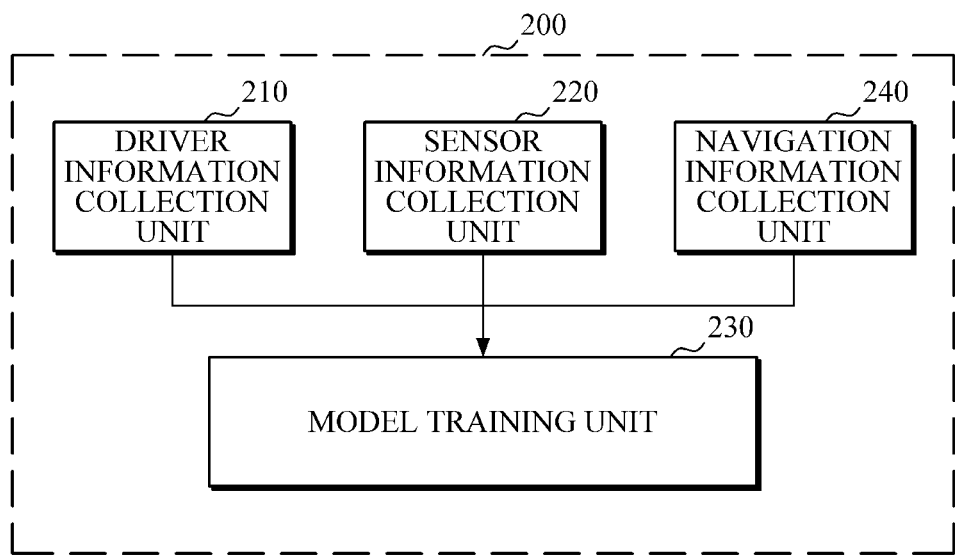
FIG. 2 is a block diagram of an apparatus to train an autonomous driving model, according to another embodiment.

FIG. 2 is a block diagram of an apparatus for training an autonomous driving model, according to another embodiment.

Referring to FIG. 2, an autonomous driving model training apparatus 200 includes a driver information collection processor 210, a sensor information collection processor 220, a model training processor 230, and a navigation information collection processor 240. The driver information collection processor 210, the sensor information collection processor 220, and the model training processor 230 have been described in detail with reference to FIG. 1.

As shown, the autonomous driving model training apparatus 200 further includes the navigation information collection processor 240 configured to collect navigation setting information, for example, information regarding a starting location, a stopover location, and an ending location.

When the navigation setting information is collected by the navigation information collection processor 240, the model training processor 230 integrally trains the autonomous driving model to learn road driving on a route from the current starting location to an ending location via a stopover location by integrally considering a variety of driver information collected by the driver information collection processor 210 and sensor information collected by the sensor information collection processor 220.

In this case, the model training processor 230 trains an autonomous driving model for each road driving route according to a starting location, a stopover location, and an ending location to establish the autonomous driving model for each road driving route.

Figure 3:
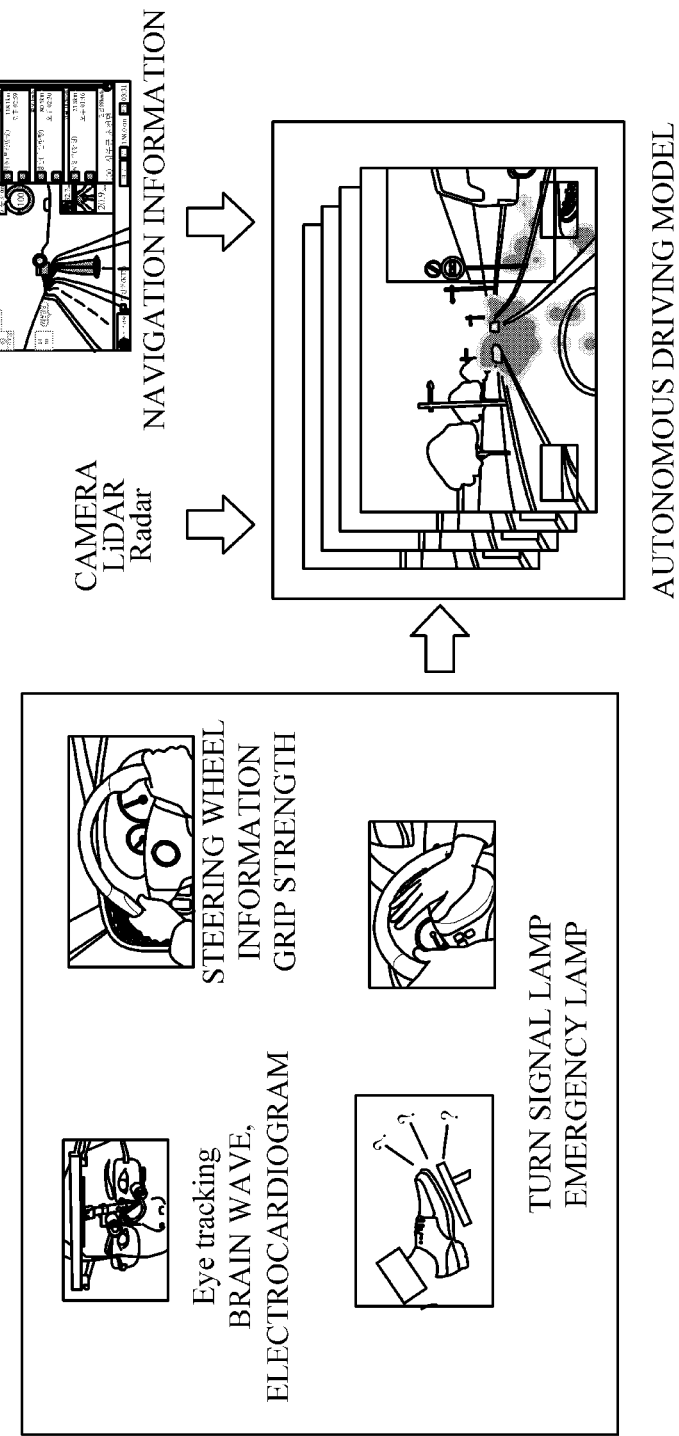
FIG. 3 is a diagram for describing acquisition of training data to train an autonomous driving model.

FIG. 3 is a diagram to describe acquisition of training data to train an autonomous driving model. As described above in detail, in order to train an autonomous driving model, according to some embodiments, navigation setting information, a variety of driver information including a gaze direction, brain wave, an electrocardiogram, steering wheel manipulation information, grip strength information, and turn-signal lamp manipulation information, and other related information may be collected in addition to sensor information regarding a camera, a lidar, a radar, etc.

In order to train an autonomous driving model that is commonly applicable to general driving, various characteristics, including gender, age, height, weight, etc., are considered when analyzing each of a plurality of drivers to collect training data as shown in FIG. 3. Also, various driving environments are preset for a plurality of drivers, and the training data is collected for each of the driving environments preset for the drivers. For this, the autonomous driving model training apparatuses 100 and 200 manage information set differently for each driver, such as driving routes, roads (including, highways, local roads, mountain trails, unpaved roads, etc.), or average speed limits or preset information such as a phone conversation or stereo manipulation after a specific location or time.

Figure 4:
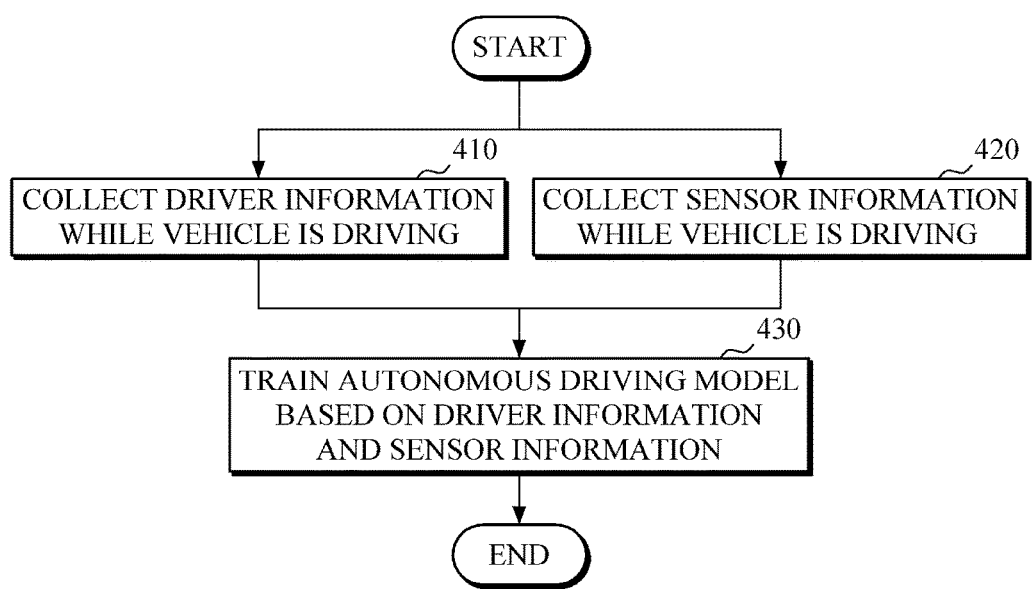
FIG. 4 is a flowchart showing a method to train an autonomous driving model, according to an embodiment.

FIG. 4 is a flowchart showing a method of training an autonomous driving model, according to an embodiment. FIG. 4 shows an example of a training method performed by the autonomous driving model training apparatus 100 of FIG. 1.

At operation 410, the autonomous driving model training apparatus 100 collects a variety of driver information associated with a driver while the vehicle is in motion or while driving the vehicle. In accord with an embodiment, as described above, the driver information includes the driving pattern information such as steering wheel manipulation information, accelerator pedal manipulation information, horn manipulation information, turn-signal lamp manipulation information, emergency button manipulation information, and brake pedal manipulation information according to various road conditions. In addition, the driver information includes driver behavior information such as stereo device manipulation, air conditioning device manipulation, or a phone conversation the driver casually or habitually does while driving. In addition, the driver information may include driver state information such as a gaze direction, a heart rate, an electrocardiogram, brain waves, grip strength of a hand holding a steering wheel, and additional information.

In addition, at operation 420, the autonomous driving model training apparatus 100 collects a variety of sensor information associated with a driving vehicle through various sensors installed in the vehicle. The information is collected in real-time in operations 410 and 420 while the vehicle is in motion. In one embodiment, operations 410 and 420 are performed simultaneously, in real-time. In another embodiment, one of the operations 410 and 420 is performed before the other.

Next, when the driver information and the sensor information are collected, at operation 430, the autonomous driving model training apparatus 100 trains an autonomous driving model in consideration of, based on, or by processing all of the collected driver information and sensor information. In this case, the autonomous driving model training apparatus 100 creates the training data consistent with various autonomous driving situations by combining pieces of the collected variety of information to train the autonomous driving model to allow accurate autonomous driving.

For example, in order to train the autonomous driving model to learn about an area in which the driver has to be careful while driving, the autonomous driving model training apparatus 100 processes gaze direction information and sensor information to create the training data. In addition, the autonomous driving model training apparatus 100 processes driving pattern information and/or driver state information to create the training data regarding a dangerous situation and a level of danger in driving.

Figure 5:
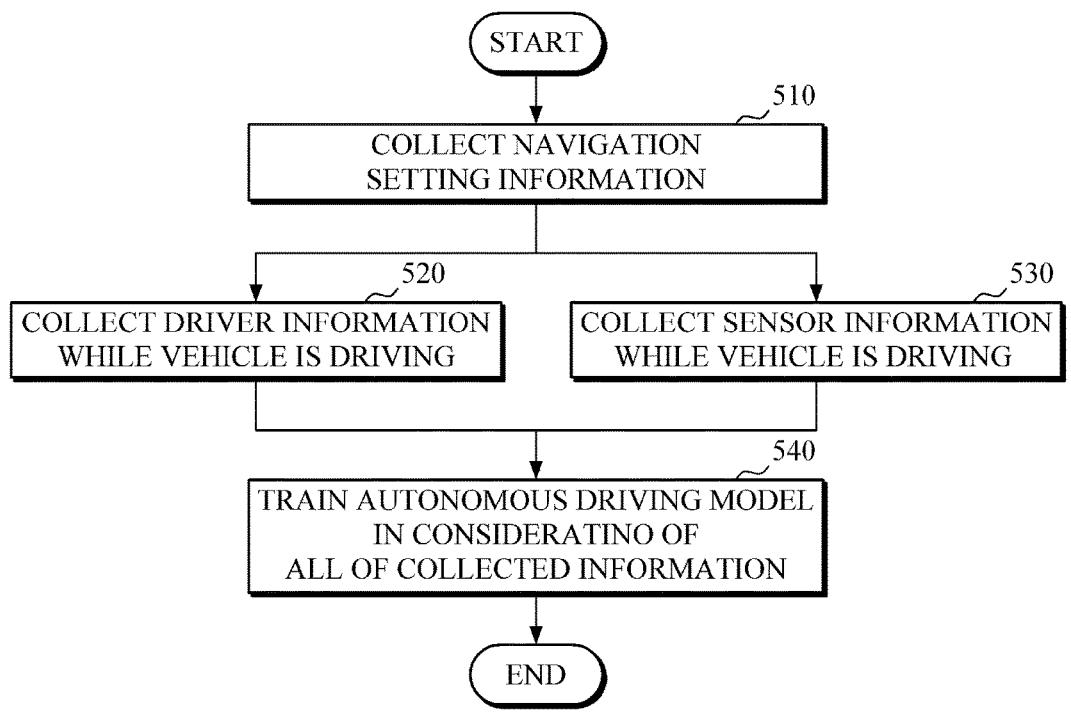
FIG. 5 is a flowchart showing a method to train an autonomous driving model, according to another embodiment.

FIG. 5 is a flowchart of a method of training an autonomous driving model, according to another embodiment. FIG. 5 shows an example of a training method performed by the autonomous driving model training apparatus 200 of FIG. 2.

At operation 510, referring to FIG. 5, the autonomous driving model training apparatus 200 may collect information set in a navigation device of a vehicle. In an embodiment, the navigation setting information includes information regarding routes along which the vehicle will drive, for example, information on a starting location, a stopover location, and an ending location.

Next, at operation 520, when the driver starts to drive the vehicle or after a predefined period of time, the autonomous driving model training apparatus 200 collects driver information associated with a driver responding to various driving situations while the vehicle is in motion.

In addition, when the vehicle is in motion, at operation 530, the autonomous driving model training apparatus 200 collects various types of sensor information generated by sensors installed in the vehicle. Here, steps 520 and 530 are performed in real time while the vehicle is in motion. In one embodiment, operations 520 and 530 are performed simultaneously, in real-time. In another embodiment, one of the operations 520 and 530 is performed before the other.

At operation 540, the autonomous driving model training apparatus 200 trains the autonomous driving model in consideration of, based on, or by processing all of the collected information.

According to this embodiment, it is possible to collect the navigation setting information, perform integrated training in consideration of a driving route of a vehicle, and train and establish an autonomous driving model for each of various driving routes.

Figure 6:
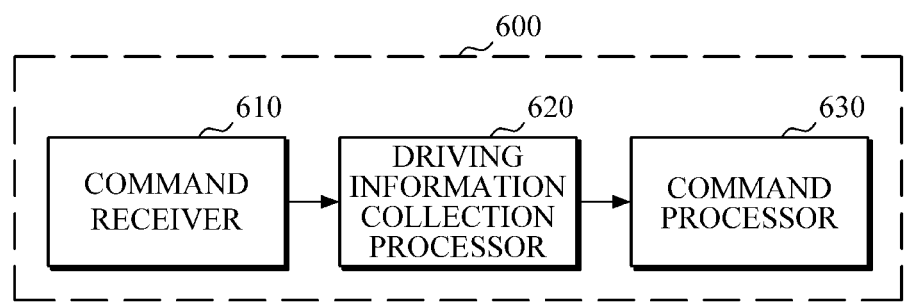
FIG. 6 is a block diagram of an autonomous driving apparatus, according to an embodiment.

FIG. 6 is a block diagram of an autonomous driving apparatus, according to an embodiment. An autonomous driving apparatus 600, according to an embodiment, is an apparatus that is installed in a vehicle and configured to support an autonomous driving of the vehicle. The autonomous driving apparatus 600 includes the above-described autonomous driving model training function.

As shown in FIG. 6, the autonomous driving apparatus 600 includes a command receiver 610, a driving information collection processor 620, and a command processor 630.

The command receiver 610 receives from a driver various autonomous driving commands that may be performed by the autonomous driving apparatus 600. For example, the autonomous driving commands include a command to switch from a manual driving mode to an autonomous driving mode or from the autonomous driving mode to the manual driving mode, a command to switch to an autonomous driving model training mode, or an end command.

When an autonomous driving command is received from the driver, the driving information collection processor 620 collects vehicle driving information so that the command processor 630 may perform an operation based on the command. In this case, the vehicle driving information is a variety of information that is created while a vehicle is driving and includes driver information associated with a particular driver, sensor information created from various types of sensors installed in the vehicle, and navigation setting information associated with a driving route, which have been created since the time at which driver entered an autonomous driving command. More detailed examples have been described above in detail, and thus detailed descriptions thereof will be omitted.

The command processor 630 processes the received autonomous driving command on the basis of the driving information collected by the driving information collection processor 620. That is, when the command is received from the driver, the command processor 630 processes the command and performs an operation corresponding to the received command in consideration of all of the collected driving information. Elements of the command processor 630 will be described in detail with reference to FIG. 7.

Figure 7:
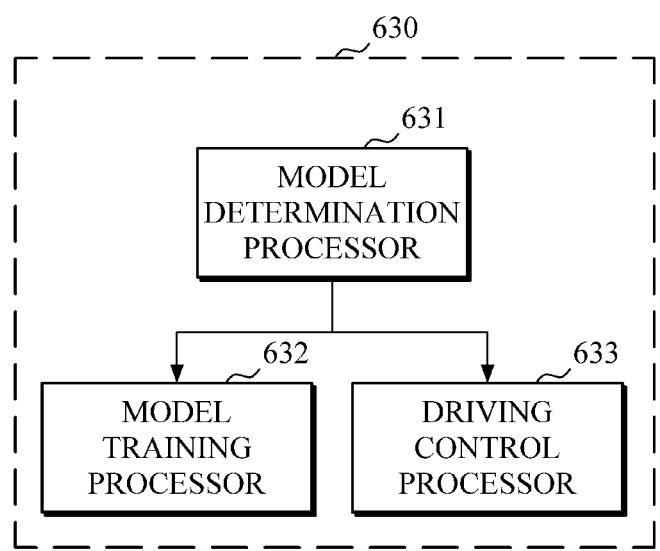
FIG. 7 is a detailed block diagram of a command processing unit described and illustrated with respect to FIG. 6.

FIG. 7 is a detailed block diagram of the command processor 630 of FIG. 6.

Referring to FIG. 7, the command processor 630 may include a model determination processor 631, a model training processor 632, and a driving control processor 633.

The model determination processor 631 processes the received command from the driver and determines an operation to be processed on the basis of a result of the processing. For example, when the autonomous driving command received from the driver is a command to switch a vehicle driving mode to an autonomous driving mode, the model determination processor 631 determines whether an autonomous driving model installed in the vehicle is appropriate before the vehicle driving mode is switched to the autonomous driving mode. In one embodiment, the model determination processor 631 determines whether an autonomous driving model installed in the vehicle is appropriate by determining whether the autonomous driving model installed in the vehicle corresponds to the driver to be driving the vehicle, based on the driving conditions, the driving location, or other information that the driver information and the sensor information and the navigation setting information include to define the model determination processor 631.

In addition, when the model determination processor 631 determines that the autonomous driving model is appropriate, the model determination processor 631 determines to process the received command to perform autonomous driving. On the other hand, when the model determination processor 631 determines that the autonomous driving model is not appropriate, the model determination processor 631 restrains from executing the autonomous driving model.

As an example, through the driver information of the driving information collected by the driving information collection processor 620, the model determination processor 631 checks whether the autonomous driving model is trained in advance or pre-trained with regards to the current driver and determines whether the autonomous driving model is appropriate for the driver when a result of the checking is that the autonomous driving model is not pre-trained for the current driver.

As another example, the model determination processor 631 checks whether the autonomous driving model is pre-trained with regards to the current driving route with reference to the navigation setting information of the driving information collected by the driving information collection processor 620. When a result of the checking is that the autonomous driving model is not pre-trained to learn about the current driving route, the model determination processor 631 determines that the autonomous driving model is not appropriate for the current driving situation.

When it is determined that the autonomous driving model is not appropriate and, thus, the autonomous driving model needs to be retrained, the model determination processor 631 confirms with the driver about whether to perform the retraining or, regardless, perform autonomous driving and determines an operation to be processed based on the driver's response to the inquiry.

When the driver purchases a new vehicle or desires to drive along a new driving route, the driver enters a command to the model determination processor 631 to operate the vehicle in a training mode in order to establish his/her suitable model. In this case, when the command received from the driver is a command to train the autonomous driving model, the model determination processor 631 skips the process of determining whether the autonomous driving model is appropriate for the current driver or driving route. However, embodiments of the present invention are not limited thereto. In some cases, the model determination processor 631 checks whether the current autonomous driving model has been recently trained even when the driver enters the training command. When the training has been recently performed, within a preset period of time, such as an hour, a day, a week, or other time period, the model determination processor 631 determines that the retraining need not be performed. In this case, the model determination processor 631 provides the driver with information indicating that additional training is not needed or request the driver to confirm whether to perform the retraining once again.

When the model determination processor 631 determines that the autonomous driving model needs to be trained, the model training processor 632 creates training data based on all of the driver information, the sensor information, and the navigation setting information collected by the driving information collection processor 620 and trains the autonomous driving model using the created training data. In this case, the model training processor 632 applies the above-described autonomous driving model training technique to train the autonomous driving model.

In order to perform the training sufficiently using the driving information, the model training processor 632 trains the autonomous driving model at a predetermined time after the command is entered from the driver. In one embodiment, the predetermine time at which the training is performed may be preset by a manufacturer when the autonomous driving apparatus 600 is installed in the vehicle.

When the model determination processor 631 determines that the command of the driver is to perform an autonomous driving, the driving control processor 633 switches a vehicle driving mode from a manual mode in which the driver manipulate a vehicle to an autonomous driving mode and automatically controls an operation of the vehicle using the driving mode collected by the driving information collection processor 620 and the autonomous driving mode.

The driving control processor 633 may automatically control the operation of the vehicle to perform an operation corresponding to the driver's habit or driving pattern according to the current driving situation by entering the navigation setting information and the sensor information collected in real-time into the autonomous driving model.

According to an embodiment, even when the vehicle operates in an autonomous driving mode, it is possible to control the operation of the vehicle similarly as in a situation in which the driver is actively driving the vehicle because the autonomous driving model is trained in consideration of the driver's habit or driving pattern.

Figure 8:
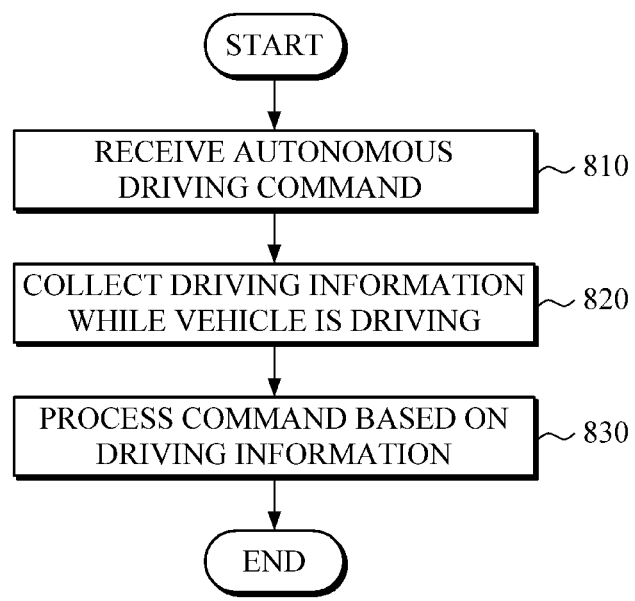
FIG. 8 is a flowchart of an autonomous driving method, according to an embodiment.

FIG. 8 is a flowchart of an autonomous driving method, according to an embodiment.

Referring to FIG. 8, at operation 810, in response to a driver entering an autonomous driving command while driving a vehicle, the autonomous driving apparatus 600 receives the command from the driver. In an embodiment, the autonomous driving command includes a command to switch to an autonomous driving mode or to a manual driving mode, a command for switching to an autonomous driving model training mode, or an end command.

At operation 820, when the autonomous driving command is received from the driver, the autonomous driving apparatus 600 collects driving information that is used to process the received command. In an embodiment, the vehicle driving information is a variety of information that is created while a vehicle is driving and includes the driver information associated with a driver, the sensor information created from various types of sensors installed in the vehicle, and the navigation setting information associated with a driving route, which have been created since or prior to the time at which driver entered an autonomous driving command.

At operation 930, the autonomous driving apparatus 600 processes a command the driver requests using the received driving information.

Figure 9:
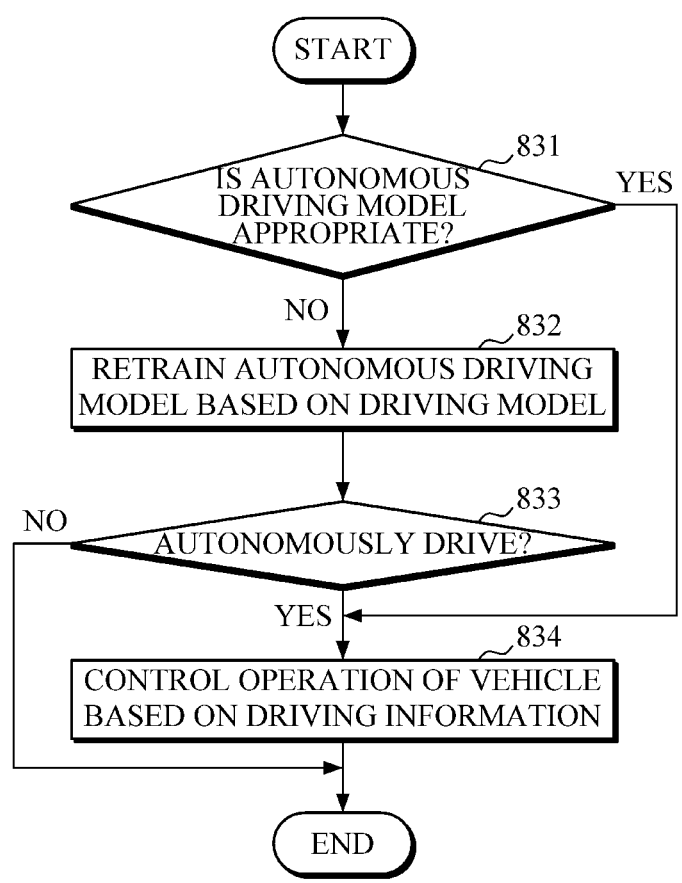
FIG. 9 is a detailed flowchart of a command processing of FIG. 8.

FIG. 9 is a detailed flowchart of the command processing operation 830 of FIG. 8. Operation 830 will be described in detail below with reference to FIGS. 8 and 9.

At operation 810, when the autonomous driving command is received from the driver, the autonomous driving apparatus 600 interprets the received command to determine, at operation 831, whether to process the received command to operate the vehicle in an autonomous driving mode, in which the driving of a vehicle is automatically controlled, or to operate the vehicle in a training mode, in which an autonomous driving model installed for autonomous driving is retrained. At operation 831, the autonomous driving apparatus 600 determines whether the current autonomous driving model applied to the vehicle is appropriate.

For example, when the autonomous driving command received from the driver is to operate the vehicle in the training mode, the autonomous driving apparatus 600 determines to operate the vehicle in the training mode. In this case, when the current autonomous driving model is one that has been recently trained, the autonomous driving apparatus 600 inquires the driver of whether to perform the training and performs the training on the basis of the driver's response to the inquiry.

On the other hand, when the autonomous driving command is to operate the vehicle in the autonomous driving mode, the autonomous driving apparatus 600 determines that an autonomous driving model to be applied is appropriate based on the driver information or the navigation setting information before operating the vehicle in the autonomous driving mode. As an example, when a driver purchases a new vehicle or when a driver is changed because an owner of the current vehicle has changed, that is, when an autonomous driving model applied to the current vehicle is not trained for a particular driver, the autonomous driving apparatus 600 determines that the autonomous driving model is not appropriate for or does not correspond to the driver driving the vehicle, or is not trained for a particular driving route or is not trained for current driving conditions. As another example, when the current autonomous driving model is not trained for a new driving route, the autonomous driving apparatus 600 determines that the autonomous driving model is not appropriate. When the autonomous driving apparatus 600 determines that the current autonomous driving model is not appropriate, the autonomous driving apparatus 600 operates the vehicle in the training mode. In this case, the autonomous driving apparatus 600 informs the driver that the vehicle will operate in the training mode and may finally determine an operation to be processed on the basis of the driver's response.

At operation 831, when the autonomous driving apparatus 600 determines that the autonomous driving model currently applied is not appropriate, at operation 832, the autonomous driving apparatus 600 trains the autonomous driving model using the collected driving information. In this case, the autonomous driving apparatus 600 uses the above-described autonomous driving model training technique and trains the autonomous driving model after driving information is collected for a predetermined time in order to perform the training using a sufficient amount of driving information.

At operation 833, in response to the training of the autonomous driving model being completed, the autonomous driving model training apparatus 200 determines whether to operate the vehicle in the autonomous driving mode. In this example, the autonomous driving apparatus 600 informs or notifies the driver that the training has been completed and inquires whether to keep performing automatic control of the driving of the vehicle or operate the vehicle in the autonomous driving mode according to a predetermined rule.

Next, in response to the autonomous driving apparatus 600 determining in operation 831 that the autonomous driving model is appropriate for or does correspond to the driver driving the vehicle, or is trained for the particular driving route or is trained for the current driving conditions or determines in operation 833 that the vehicle is operating in the autonomous driving mode, at operation 834, the autonomous driving apparatus 600 automatically controls an operation of the vehicle using the autonomous driving mode and the driving information collected, in real-time, in operation 820.

The driver information collection processor 110 and 210, the sensor information collection processor 120 and 220, the model training processor 130 and 230, the navigation information collection processor 240, the command receiver 610, the driving information collection processor 620, the command processor 630, model determination processor 631, the model training processor 632, and the driving control processor 633 in FIGS. 1-3 and 6-7 that perform the operations described in this application are implemented by hardware components configured to perform the operations described in this application that are performed by the hardware components. Examples of hardware components that may be used to perform the operations described in this application where appropriate include controllers, sensors, generators, drivers, memories, comparators, arithmetic logic units, adders, subtractors, multipliers, dividers, integrators, and any other electronic components configured to perform the operations described in this application. In other examples, one or more of the hardware components that perform the operations described in this application are implemented by computing hardware, for example, by one or more processors or computers. A processor or computer may be implemented by one or more processing elements, such as an array of logic gates, a controller and an arithmetic logic unit, a digital signal processor, a microcomputer, a programmable logic controller, a field-programmable gate array, a programmable logic array, a microprocessor, or any other device or combination of devices that is configured to respond to and execute instructions in a defined manner to achieve a desired result. In one example, a processor or computer includes, or is connected to, one or more memories storing instructions or software that are executed by the processor or computer. Hardware components implemented by a processor or computer may execute instructions or software, such as an operating system (OS) and one or more software applications that run on the OS, to perform the operations described in this application. The hardware components may also access, manipulate, process, create, and store data in response to execution of the instructions or software. For simplicity, the singular term "processor" or "computer" may be used in the description of the examples described in this application, but in other examples multiple processors or computers may be used, or a processor or computer may include multiple processing elements, or multiple types of processing elements, or both. For example, a single hardware component or two or more hardware components may be implemented by a single processor, or two or more processors, or a processor and a controller. One or more hardware components may be implemented by one or more processors, or a processor and a controller, and one or more other hardware components may be implemented by one or more other processors, or another processor and another controller. One or more processors, or a processor and a controller, may implement a single hardware component, or two or more hardware components. A hardware component may have any one or more of different processing configurations, examples of which include a single processor, independent processors, parallel processors, single-instruction single-data (SISD) multiprocessing, single-instruction multiple-data (SIMD) multiprocessing, multiple-instruction single-data (MISD) multiprocessing, and multiple-instruction multiple-data (MIMD) multiprocessing.

The methods illustrated in FIGS. 4-5 and 8-9 that perform the operations described in this application are performed by computing hardware, for example, by one or more processors or computers, implemented as described above executing instructions or software to perform the operations described in this application that are performed by the methods. For example, a single operation or two or more operations may be performed by a single processor, or two or more processors, or a processor and a controller. One or more operations may be performed by one or more processors, or a processor and a controller, and one or more other operations may be performed by one or more other processors, or another processor and another controller. One or more processors, or a processor and a controller, may perform a single operation, or two or more operations.

Instructions or software to control computing hardware, for example, one or more processors or computers, to implement the hardware components and perform the methods as described above may be written as computer programs, code segments, instructions or any combination thereof, for individually or collectively instructing or configuring the one or more processors or computers to operate as a machine or special-purpose computer to perform the operations that are performed by the hardware components and the methods as described above. In one example, the instructions or software include machine code that is directly executed by the one or more processors or computers, such as machine code produced by a compiler. In another example, the instructions or software includes higher-level code that is executed by the one or more processors or computer using an interpreter. The instructions or software may be written using any programming language based on the block diagrams and the flow charts illustrated in the drawings and the corresponding descriptions in the specification, which disclose algorithms for performing the operations that are performed by the hardware components and the methods as described above.

The instructions or software to control computing hardware, for example, one or more processors or computers, to implement the hardware components and perform the methods as described above, and any associated data, data files, and data structures, may be recorded, stored, or fixed in or on one or more non-transitory computer-readable storage media. Examples of a non-transitory computer-readable storage medium include read-only memory (ROM), random-access memory (RAM), flash memory, CD-ROMs, CD-Rs, CD+Rs, CD-RWs, CD+RWs, DVD-ROMs, DVD-Rs, DVD+Rs, DVD-RWs, DVD+RWs, DVD-RAMs, BD-ROMs, BD-Rs, BD-R LTHs, BD-REs, magnetic tapes, floppy disks, magneto-optical data storage devices, optical data storage devices, hard disks, solid-state disks, and any other device that is configured to store the instructions or software and any associated data, data files, and data structures in a non-transitory manner and provide the instructions or software and any associated data, data files, and data structures to one or more processors or computers so that the one or more processors or computers can execute the instructions. In one example, the instructions or software and any associated data, data files, and data structures are distributed over network-coupled computer systems so that the instructions and software and any associated data, data files, and data structures are stored, accessed, and executed in a distributed fashion by the one or more processors or computers.

While this disclosure includes specific examples, it will be apparent after an understanding of the disclosure of this application that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner, and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:

1. An apparatus to train an autonomous driving model, the apparatus comprising:
    a driver information collection processor configured to collect driver information while a vehicle is being driven by a driver;
    a sensor information collection processor configured to collect sensor information from a sensor installed in the vehicle while the vehicle is being driven;
    a model training processor configured to train the autonomous driving model based on the driver information and the sensor information; and
    a model determination processor configured to determine whether the autonomous driving model is appropriate for the driver or a current driving situation based on either one or both of the driver information or navigation setting information comprising information on a starting location and an ending location.

2. The apparatus of claim 1, wherein the vehicle is driven in at least one of a real-road driving situation and a virtual driving situation.

3. The apparatus of claim 1, wherein the driver information comprises at least one of driver state information, driver behavior information, and driving pattern information.

4. The apparatus of claim 3, wherein,
    the driver state information comprises at least one of information about a gaze direction, a heart rate, an electrocardiogram, and brain waves of a driver, and grip strength of the driver's hand holding a steering wheel,
    the driver behavior information comprises at least one of information about manipulation of a stereo device, air conditioning device, a mirror device, and a navigation device installed in the vehicle, and
    the driving pattern information comprises at least one of information about a steering wheel manipulation information, horn manipulation information, turn-signal manipulation information, emergency button manipulation information, and brake pedal manipulation information.

5. The apparatus of claim 4, wherein the model training processor trains the autonomous driving model to learn about a driving area based on information about the gaze direction of the driver and trains the autonomous driving model to learn at least one of a dangerous situation and a level of danger in driving based on the driving pattern information.

6. The apparatus of claim 1, wherein the model training processor trains the autonomous driving model to learn about an integrated driving situation from the starting location to the ending location and based on the navigation setting information.

7. The apparatus of claim 1, wherein the sensor information comprises at least one of surrounding image information, surrounding voice information, current location information, light detection and ranging (lidar) sensor information, radar sensor information, vehicle speed information, and acceleration information.

8. The apparatus of claim 1, wherein the autonomous driving model is based on a deep neural network configured to learn spatial information and temporal information.

9. A method to train an autonomous driving model, the method comprising:
    collecting driver information while a vehicle is being driven by a driver;
    collecting sensor information from a sensor installed in the vehicle while the vehicle is being driven;
    training the autonomous driving model based on the driver information and the sensor information; and
    determining whether the autonomous driving model is appropriate for the driver or a current driving situation based on either one or both of the driver information or navigation setting information comprising information on a starting location and an ending location.

10. The method of claim 9, wherein the driver information comprises at least one of driver state information, driver behavior information, and driving pattern information.

11. The method of claim 10, wherein,
    the driver state information comprises at least one of information about a gaze direction, a heart rate, an electrocardiogram, and brain waves of a driver, and grip strength of the driver's hand holding a steering wheel,
    the driver behavior information comprises at least one of information about manipulation of a stereo device, air conditioning device, a mirror device, and a navigation device installed in the vehicle, and the driving pattern information comprises at least one of a steering wheel manipulation information, horn manipulation information, turn-signal manipulation information, emergency button manipulation information, and brake pedal manipulation information.

12. The method of claim 11, wherein the training of the model comprises training the autonomous driving model to learn about a driving area based on information about the gaze direction of the driver and training the autonomous driving model to learn about at least one of a dangerous situation and a level of danger in driving based on the driving pattern information.

13. The method of claim 9, wherein the training of the model comprises training the autonomous driving model to learn about an integrated driving situation from the starting location to the ending location further based on the navigation setting information.

14. The method of claim 9, wherein the sensor information comprises at least one of surrounding image information, surrounding voice information, current location information, light detection and ranging (lidar) sensor information, radar sensor information, vehicle speed information, and acceleration information.

15. A non-transitory computer-readable storage medium storing instructions that, when executed by a processor, cause the processor to perform the method of claim 9.

16. An autonomous driving apparatus, comprising:
a driving information collection processor configured to collect vehicle driving information comprising at least one of driver information, sensor information, and navigation setting information while a vehicle is being driven;
a command receiver configured to receive an autonomous driving command from a driver; and
a command processor configured to
train an autonomous driving model installed in the vehicle or autonomously drive the vehicle based on the collected driving information, and
determine whether to execute the autonomous driving command based on the autonomous driving model.

17. The autonomous driving apparatus of claim 16, wherein the command processor comprises:
a model determination processor configured to determine whether the autonomous driving model is appropriate for a driver and the current driving situation based on either one or both of the driver information and the navigation setting information;
a model training processor configured to retrain the autonomous driving model based on the collected driving information upon determining that the autonomous driving model is inappropriate; and
a driving control processor configured to automatically control operation of the vehicle using the collected driving information and the autonomous driving model upon determining that the autonomous driving model is appropriate.

18. The autonomous driving apparatus of claim 17, wherein the model determination processor checks whether the autonomous driving model is trained to learn about the driver based on the driver information and determines that the autonomous driving model is inappropriate upon determining that the autonomous driving model is untrained about the driver.

19. The autonomous driving apparatus of claim 18, wherein the model determination processor checks whether the autonomous driving model is trained to learn about a driving route from a starting location to an ending location based on the navigation setting information and determines that the autonomous driving model is inappropriate upon determining that the autonomous driving model is untrained about the driving route.

20. An apparatus, comprising:
a processor configured to
collect driver information corresponding to behavior information of a driver driving a vehicle, virtually or in real-time,
collect sensor information from sensors capturing either one or both of image and ambient information surrounding the vehicle and vehicle operational parameters corresponding to either one or both of a current driving route and current driving conditions,
train an autonomous driving model by combining the driver information and the sensor information, and
execute the autonomous driving model upon determining that the trained autonomous driving model corresponds to at least one of the driver or the current driving route.

21. The apparatus of claim 20, wherein the processor comprises:
a driver information collection processor configured to collect the driver information,
a sensor information collection processor configured to collect the sensor information corresponding to either one or both of the current driving route and the current driving conditions,
a model training processor configured to train the autonomous driving model, and
a driving control processor configured to execute the autonomous driving model upon determining that the trained autonomous driving model corresponds to at least one of the driver, the current driving route.

22. The apparatus of claim 20, further comprising:
a navigation information collection processor configured to collect navigation setting information comprising information regarding a starting location, a stopover location, and an ending location.

23. The apparatus of claim 20, wherein the processor is further configured to check whether the autonomous driving model has been trained within a preset period of time to prevent a retraining of the autonomous driving model.

24. The apparatus of claim 1, further comprising:
a model training processor configured to retrain the autonomous driving model based on the collected driving information upon determining that the autonomous driving model is inappropriate; and
a driving control processor configured to automatically control operation of the vehicle using the collected driving information and the autonomous driving model upon determining that the autonomous driving model is appropriate.

25. The apparatus of claim 24, wherein the driving control processor is further configured to:
upon determining by the model determination processor that the autonomous driving model is inappropriate, request the driver to confirm whether to retrain the autonomous driving model.

* * * * *